United States Patent
Alves Fortunato et al.

(10) Patent No.: US 10,564,141 B2
(45) Date of Patent: Feb. 18, 2020

(54) METHOD FOR CONTINUOUSLY MONITORING THE DEGREE OF PROGRESS OF OXIDATION OF A FUEL

(71) Applicant: IFP Energies nouvelles, Rueil-Malmaison (FR)

(72) Inventors: Maira Alves Fortunato, Carrieres sur Seine (FR); Arij Ben Amara, Le Pecq (FR); Nicolas Jeuland, Antony (FR); Laurie Starck, Rueil Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 15/571,762

(22) PCT Filed: May 4, 2016

(86) PCT No.: PCT/EP2016/060101
§ 371 (c)(1),
(2) Date: Nov. 3, 2017

(87) PCT Pub. No.: WO2016/177838
PCT Pub. Date: Nov. 10, 2016

(65) Prior Publication Data
US 2018/0143175 A1   May 24, 2018

(30) Foreign Application Priority Data
May 5, 2015   (FR) ..................... 15 54011

(51) Int. Cl.
*G01N 33/28* (2006.01)
*G01N 21/3504* (2014.01)
(Continued)

(52) U.S. Cl.
CPC ..... *G01N 33/2805* (2013.01); *G01N 21/3504* (2013.01); *G01N 27/026* (2013.01);
(Continued)

(58) Field of Classification Search
CPC .......... G01N 33/2805; G01N 21/3504; G01N 27/026; G01N 33/225; G01N 33/28; G01N 33/2829; G01N 2030/025
See application file for complete search history.

(56) References Cited

U.S. PATENT DOCUMENTS 3,670,561 A * 6/1972 Hundere ............ G01N 15/0618
                                                    73/61.62
5,101,658 A * 4/1992 Wilson, III ........ G01N 33/2805
                                                    374/43
(Continued)

FOREIGN PATENT DOCUMENTS

JP    2008-281486 A    11/2008
WO    94/17391 A1      8/1994
(Continued)

OTHER PUBLICATIONS

Arunas Andziulis, "Long Term Oxidation Stability of Gasoline on Account of MIR Monitoring", Transport, pp. 218-222, 2006. (Year: 2006).*

(Continued)

*Primary Examiner* — David A Rogers
(74) *Attorney, Agent, or Firm* — Fitch, Even, Tabin & Flannery, L.L.P.

(57) ABSTRACT

The present invention relates to a method for continuously monitoring the degree of progress of oxidation of a fuel, comprising at least the following steps:
  determining at least one indicator for the progress of the oxidation reaction to be monitored,
  measuring the content of said indicator for the progress of the oxidation reaction in said fuel,
  classifying the degree of progress of oxidation of said fuel, (Continued)

Retention time (min)

determining the measures to be taken as a function of said classification.

15 Claims, 2 Drawing Sheets

(51) Int. Cl.
    *G01N 27/02* (2006.01)
    *G01N 33/22* (2006.01)
    *G01N 30/02* (2006.01)

(52) U.S. Cl.
    CPC ....... *G01N 33/225* (2013.01); *G01N 33/2829* (2013.01); *G01N 2030/025* (2013.01)

(56) References Cited

U.S. PATENT DOCUMENTS

| | | | |
|---|---|---|---|
| 5,163,982 A | 11/1992 | de Andrade Brüning | |
| 5,223,718 A * | 6/1993 | Taboada | G01N 21/64 250/458.1 |
| 5,287,731 A * | 2/1994 | Florkowski | G01N 33/2805 422/53 |
| 5,337,599 A * | 8/1994 | Hundere | G01N 33/2805 374/43 |
| 5,475,612 A | 12/1995 | Espinosa et al. | |
| 6,127,185 A * | 10/2000 | Melton | G01N 27/06 324/71.1 |
| 7,078,910 B2 | 7/2006 | Hirthe | G01N 33/2888 324/446 |
| 7,093,481 B2 * | 8/2006 | Morris | G01N 33/2805 29/90.01 |
| 7,257,987 B2 * | 8/2007 | O'Brien | G01N 1/2202 73/23.22 |
| 7,391,035 B2 * | 6/2008 | Kong | G01N 21/6408 250/461.1 |
| 8,066,960 B2 * | 11/2011 | Handschuck | G01N 33/2805 422/522 |
| 8,549,897 B2 * | 10/2013 | Lesieur | G01N 33/2888 73/53.06 |
| 9,678,001 B2 * | 6/2017 | Zhao | G01N 33/28 |
| 10,209,201 B2 * | 2/2019 | Cadieux, Jr. | G01N 21/88 |
| 2005/0088646 A1 * | 4/2005 | Kong | G01N 21/643 356/70 |
| 2007/0187617 A1 | 8/2007 | Kong et al. | |
| 2008/0022757 A1 * | 1/2008 | Zhou | G01N 33/2805 73/53.05 |
| 2008/0167823 A1 | 7/2008 | Koehler et al. | |
| 2009/0001961 A1 * | 1/2009 | Lin | G01N 33/2829 324/71.1 |
| 2009/0115435 A1 * | 5/2009 | Tomlinson | G01N 33/2829 324/698 |
| 2011/0016954 A1 * | 1/2011 | Lesieur | G01N 33/2805 73/53.05 |

FOREIGN PATENT DOCUMENTS

| | | |
|---|---|---|
| WO | 2008/080108 A1 | 7/2008 |
| WO | 2009/080049 A1 | 7/2009 |
| WO | 2013/154175 A1 | 10/2013 |
| WO | 2014/085009 A1 | 6/2014 |

OTHER PUBLICATIONS

Bacha et al., "Original Experimental Approach for Assessing Transport Fuel Stability", Journal of Visualized Experiments, No. 116, Oct. 21, 2016. (Year: 2016).*

International Search Report for PCT/EP2016/060101, dated Jun. 17, 2016; English translation submitted herewith (7 pgs.).

Svilans et al., Spectroscopic Monitoring of Biodiesel Aging, Material Science and Applied Chemistry, 2013.

* cited by examiner

METHOD FOR CONTINUOUSLY MONITORING THE DEGREE OF PROGRESS OF OXIDATION OF A FUEL

CROSS-REFERENCE TO RELATED APPLICATIONS

This application is a U.S. national phase application filed under 35 U.S.C. § 371 of International Application No. PCT/EP2016/060101, filed May 4, 2016, designating the United States, which claims priority from French Patent Application No. 15/54.011, filed May 5, 2015, which are hereby incorporated herein by reference in their entirety.

FIELD OF THE INVENTION

Changes in the environmental, economic and regulatory context have favoured the emergence of alternative biofuels and fuels in middle distillates such as kerosenes and fuel oils.

These changes are in respect of both the formulations for the fuels, the logistics and the associated applications. However, they are accompanied by problems with degradation of the fuels which arise more frequently. Alternative fuels based on fatty acid methyl esters (FAME) used in particular as a biofuel provide less stable components which facilitate the phenomena of autoxidation and deposit formation in the fuel circuits.

The formation of these deposits and lacquers from autoxidation of the fuel is critical in the aeronautical and terrestrial transport industries. These lacquers may in fact bring about major failures in engines and turbines and are therefore critical as regards the safety of users. Thus, it is of fundamental importance to be able to accurately determine the degree of oxidation of a fuel, whether it is of fossil origin or obtained from biomass, in order to be able to avoid the use of fuels with a degree of oxidation which could favour these phenomena.

PRIOR ART

Patent application WO 14/085009 discloses a model which can be used to prepare a kerosene type fuel which has a thermal break point which can be envisaged as a function of its initial composition in terms of sulphur-containing compounds, nitrogen-containing compounds, aromatic compounds and density. The method described is based on a Fourier transform ion cyclotron resonance-mass spectroscopy (FTICR-MS) type characterization, inter alia, of aeronautical kerosenes in order to determine their thermal stability.

Patent application US 2008/167823 describes a method for measuring the variation in the concentration of esters or the presence of fatty acids, glycerides or methanol by using impedance spectroscopy. The method described can be used to measure the concentration of fatty acid methyl ester (FAME) in a diesel or kerosene type fuel and also to measure the acid number (total acid number: TAN), which is considered to be an indicator of the stability and degradation of the fuels.

The U.S. Pat. No. 5,163,982 describes a method for detecting the presence of polar species, based on reverse phase gas phase chromatography (GC) which can be used to determine and classify the stability of fuels by a comparative method.

Patent application WO 09/080049 proposes an on-line or at-line measurement method (near infrared, fluorescence) and for correlation using a chemometric method with the characteristics of the fuel, including TAN, in order to predict the properties and qualities of a fuel during the preparation thereof.

The U.S. Pat. No. 5,475,612 and patent application WO 94/17391 propose a method for predicting the properties of a fuel by means of a correlation between the infrared spectrum of said fuel and its physico-chemical properties, one possible application being the prediction of research octane number (RON) or cetane index type properties of a fuel.

Spectrometry in general, and in particular infrared spectroscopy (IR), can be used to correlate the spectra obtained with the properties of a fuel. The properties which are routinely determined in this regard are the density, viscosity or in fact the octane number. The stability to oxidation and the degree of progress of the oxidation of a fuel are not determined by these conventional techniques of analytical chemistry.

As an example, in the aeronautical field the thermal stability and the stability to oxidation of a fuel are generally determined by using the method known as the jet fuel thermal oxidation tester (JFTOT), which provides a "pass or fail" result.

Currently, for the majority, the methods for the characterization and stability to oxidation of fuels are based on an accelerated oxidation of the product at temperature while monitoring the oxidation by the consumption of oxygen or by characterization of the products formed or by a change in a property (acid number, conductivity, etc). However, these methods cannot be used to provide a reliable correlation between the potential for lacquer formation and the actual status of the degree of oxidation of the fuel at a given time. Thus, it is often necessary to couple several methods together in order to provide an exhaustive picture.

Furthermore, several analytical techniques such as Fourier transform infrared (FTIR), gas phase chromatography (GC) or in fact impedance spectroscopy have been proposed in order to determine the stability of a fuel. However, these techniques can only provide a measurement of the initial state or the state at a time t. To our knowledge, only the patent application WO 09/080049 proposes a continuous monitoring method which can be carried out within a fuel production process.

Thus, it would be highly advantageous to develop a method which could be used to monitor the degradation of fuels continuously and alert the user in the case of severe degradation, being based on the change in the chemical composition of these fuels during use and as a function of temperature.

The Applicant has been able to develop an innovative method of this type which can be used to continuously monitor the change in a fuel with the aim of determining, at any time, whether the composition and the quality of said fuel is sufficiently sustained to be able to use it.

Aim of the Invention

In particular, the present invention concerns a method for continuously monitoring the degree of progress of oxidation of a fuel, comprising at least the following steps:

a) determining at least one indicator for the progress of the oxidation reaction to be monitored, b) measuring the content of said indicator for the progress of the oxidation reaction in said fuel, c) classifying the degree of progress of oxidation of said fuel, d) determining the measures to be taken as a function of said classification, characterized in that said progress indicator is at least one intermediate or final product or at least one co-product of at least one of the oxidation reactions with one or more components of the fuel, and in that the classification is carried out by comparison between said measured contents of said progress indicator and the contents of said progress indicator present in said fuel after a period of accelerated oxidation, measured in accordance with the method EN 15751 (or EN14112, ASTM D6751) in order to determine the induction period (IP) for said fuel, said degree of progress of oxidation then being:

initial if said measured contents correspond to an oxidation period (P1) strictly less than 0.5 IP (0 IP≤P1≤0.5 IP), intermediate if said measured contents correspond to an oxidation period (P2) of greater than or equal to 0.5 IP and strictly less than 1 IP (0.5 IP≤P2<IP), advanced if said measured contents correspond to an oxidation period (P3) of 1 IP or higher (1 IP≤P3).

The term "oxidation period" means the duration during which the fuel has theoretically undergone an oxidation compared with the reference method for determining the IP.

Thus, the method in accordance with the invention presents a complementary and different approach to discerning the quality of a fuel compared with the current state of the art, by means of a determination of the degree of progress of said fuel.

One advantage of the present invention is that it can be used to monitor the degradation of fuels continuously and alert the user in the case of severe degradation, by being based on the change in the chemical composition of these fuels during use and as a function of temperature.

Another advantage of the present invention is that of providing an innovative method for determining the degree of degradation of a fuel, based on the continuous monitoring of various molecules or families of molecules which are representative of a degree of progress of oxidation in the liquid phase and in the gas phase.

Furthermore, the method in accordance with the present invention can advantageously be used to measure the degree of progress of oxidation of a fuel in the logistical phase or in the on-board storage phase.

DETAILED DESCRIPTION OF THE INVENTION

Figure 1:
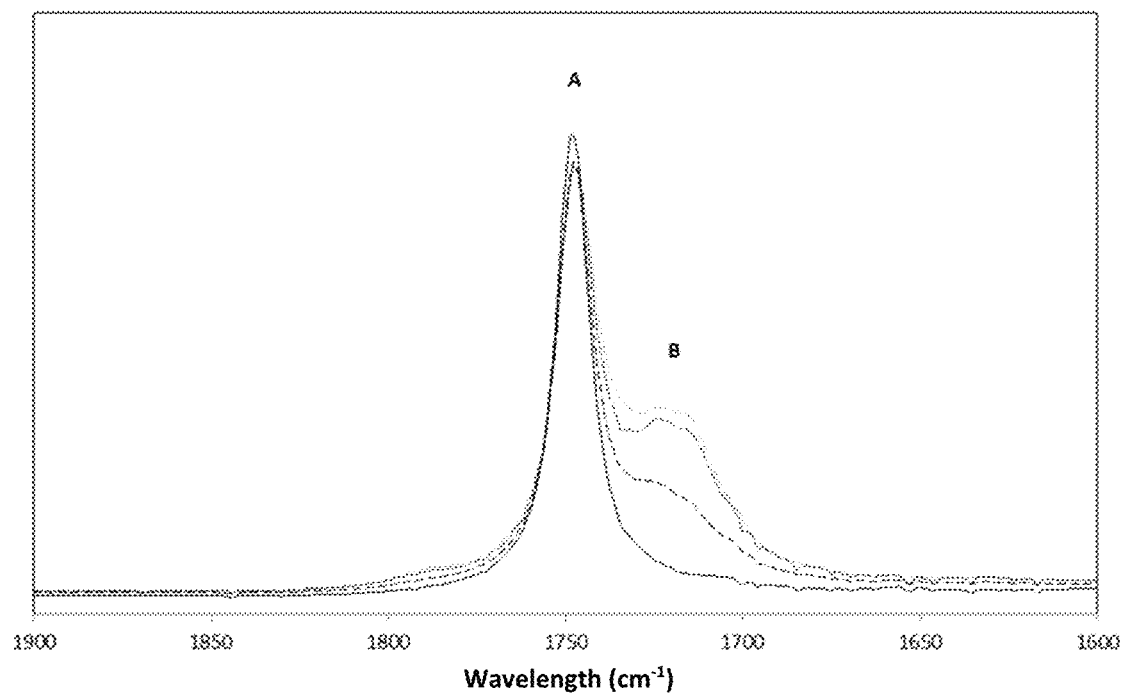
FIG. 1 shows superimposed infrared spectra demonstrating the change in the state of a fresh model fuel following various oxidation periods.

Throughout the remainder of the text, the degree of progress of oxidation will be defined as follows: initial phase, intermediate phase and advanced phase. The oxidation reactions of fuels have complex chemical kinetics with multiple reaction intermediates. These reaction intermediates are indicators of the degree of progress of said oxidation reactions.

The degree of progress of an oxidation reaction is thus directly correlated with the quantity of reaction intermediates, co-products and to the quantity of final products, said products resulting from at least one of the oxidation reactions with one or more components of the fuel, since the chemical composition of the fuel varies as a function of its degree of oxidation. Thus, it is possible to determine whether a fuel is in the initial oxidation phase, in the intermediate oxidation phase or in the advanced oxidation phase by determining the contents of said reaction intermediates, said co-products and/or said final products.

Thus, the present invention concerns a method for continuously monitoring the degree of progress of oxidation of a fuel, comprising at least the following steps:

a) determining at least one indicator for the progress of the oxidation reaction to be monitored, b) measuring the content of said indicator for the progress of the oxidation reaction in said fuel, c) classifying the degree of progress of oxidation of said fuel, d) determining the measures to be taken as a function of said classification, characterized in that said progress indicator is at least one intermediate or final product or at least one co-product of at least one of the oxidation reactions with one or more components of the fuel, and in that the classification is carried out by comparison between said measured contents of said progress indicator and the contents of said progress indicator present in said fuel after a period of accelerated oxidation, measured in accordance with the method EN 15751 (or EN14112, ASTM D6751) in order to determine the induction period (IP) for said fuel, said degree of progress of oxidation then being:

initial if said measured contents correspond to an oxidation period (P1) strictly less than 0.5 IP (0 IP≤P1≤0.5 IP), intermediate if said measured contents correspond to an oxidation period (P2) of greater than or equal to 0.5 IP and strictly less than 1 IP (0.5 IP≤P2<IP), advanced if said measured contents correspond to an oxidation period (P3) of 1 IP or higher (1 IP≤P3).

The method in accordance with the present invention is advantageously applicable to any fuel of fossil origin or obtained from biomass.

In one preferred embodiment, the fuel is selected from kerosene, gas oil and gasoline.

The method in accordance with the present invention may advantageously be used to measure the degree of progress of oxidation of a fuel in the logistical phase or in the on-board storage phase.

The term "logistical phase" means the series of phases during the course of which a fuel is not in a reservoir of a motorized vehicle.

The term "on-board storage phase" means the series of phases during the course of which a fuel is in a reservoir of a motorized vehicle, whether or not the engine is running.

In accordance with the invention, the method comprises a step a) for determining at least one indicator for the progress of the oxidation reaction to be monitored.

In accordance with the invention, said progress indicator is an intermediate product, a final product or a co-product of at least one of the oxidation reactions with one or more components of the fuel.

The oxidation of hydrocarbons leads inevitably to the formation of molecules carrying at least one oxygenated function. Depending on the degree of progress of the oxidation, the molecules will carry functions containing greater or lesser numbers of oxygen atoms. As an example, a carboxylic acid type function which comprises two oxygen atoms is obtained from the oxidation of an aldehyde function which contains a single oxygen atom. Monitoring the formation and change in the molecules carrying at least one oxygenated function within a fuel can thus be used to determine the degree of oxidation of said fuel.

The progress indicator is advantageously one or more molecules belonging to families carrying at least one oxygenated function or in fact the distribution of molecular weights of one or more polymerized molecules obtained from monomers belonging to these families.

In a first embodiment, the progress indicator is preferably one or more molecules belonging to families selected from aldehydes, alcohols, ketones, ketoacids, epoxides and carboxylic acids.

The molecules comprising said fuel before oxidation preferably belong to the family of linear or branched alkanes, linear or branched alkenes or the aromatics family.

Preferably, said progress indicator is a specific molecule belonging to the families defined above.

In the case in which the progress indicator is a molecule belonging to the aldehyde family, the progress indicator is selected from formaldehyde and acetaldehyde.

In the case in which the progress indicator is a molecule belonging to the alcohol family, the progress indicator is methanol.

In the case in which the progress indicator is a molecule belonging to the epoxide family, the progress indicator is ethylene oxide.

Alternatively, the progress indicator is one or more co-product(s) obtained from the various oxidation reactions that said fuel may be subjected to.

In the case in which the progress indicator is one or more co-products, said progress indicator is advantageously one or more polymerized molecules obtained from one or more monomers.

Preferably, said monomers belong to the families of linear or branched alkenes, aromatics, aldehydes, alcohols, ketones, ketoacids, epoxides and carboxylic acids.

In the case in which said monomer belongs to the family of aldehydes, the monomer is preferably selected from formaldehyde and acetaldehyde.

In the case in which said monomer belongs to the family of alcohols, the monomer is preferably methanol.

In the case in which said monomer belongs to the family of epoxides, the monomer is preferably ethylene oxide.

In the case in which said monomer belongs to the family of peroxides, the monomer is preferably selected from peroxides, alkoxides of radical species of said fuel ($RO_2°$, $RO°$, $R°$).

In accordance with the invention, the method comprises a step b) for measuring the content of said progress indicator for the oxidation reaction in said fuel.

In one embodiment, said measurement of the content of at least one progress indicator is carried out by means of at least one analytical method which is known to the person skilled in the art, such as by ultraviolet analysis (UV), infrared analysis (IR), gas phase chromatography (GC), mass spectrometry (MS), small angle X ray diffusion (SAXS) or in fact by tonometry.

In accordance with the invention, the method comprises a step c) for the classification of the degree of progress of oxidation of said fuel.

In accordance with the invention, the classification is carried out by comparison between said measured contents of said progress indicator and the contents of said progress indicator present in said fuel after a period of accelerated oxidation, measured in accordance with the method EN 15751 (EN14112, ASTM D 6751), in order to determine the induction period (IP) for said fuel.

The induction period or IP is the time necessary for the fuel to reach a defined degree of oxidation. Depending on their destination and their field of use, the fuels must have an IP which is above a certain length of time in order to comply with minimum specifications.

In the standard method EN 15751, air (10 L/h) is bubbled through a 7.5 g sample of fuel at a specific temperature of (383K). The air which leaves the sample is trapped in a flask containing distilled water, where the conductivity is measured. The increase in conductivity of the cell indicates an accumulation of volatile acids in the water due to oxidation of the sample. The IP is characterized by a change in the slope for the conductimetry of the distilled water.

In accordance with the invention, said degree of progress of the oxidation of said fuel is expressed as a function of the IP and is qualified as follows:

initial if said measured contents correspond to an oxidation period (P1) strictly less than 0.5 IP (0 IP≤P1<0.5 IP), intermediate if said measured contents correspond to an oxidation period (P2) of greater than or equal to 0.5 IP and strictly less than 1 IP (0.5 IP≤P2<IP), advanced if said measured contents correspond to an oxidation period (P3) of 1 IP or higher (1 IP≤P3).

The induction period thus represents the limits defining the three degrees of oxidation of the classification in accordance with the invention. As an example, if the measured content of the progress indicator or indicators shows that the composition of said fuel corresponds to an oxidation period strictly below 0.5 IP, then the fuel will be classified as being in the initial oxidation phase.

In accordance with the invention, the method comprises a step d) for determining the actions to be carried out as a function of said classification. The user is informed of the degree of degradation of the fuel and, if appropriate, of the preventative or curative actions to be taken. When the fuel is in the initial oxidation phase, said actions to be taken are advantageously corrective actions such as the addition of an anti-oxidizing additive or, as is preferable, preventative such as eliminating pro-oxidizing sources.

Said anti-oxidizing additive is advantageously selected from butyl hydroxytoluene (BHT), 2,4-di-tert-butylphenol (2,4-DTBP), 2-tert-butyl-4-methylphénol (TBMP) and triphenylphosphine (TPP).

Examples of said pro-oxidizing sources may be aeration which is too strong, luminosity which is too high or in fact the presence of a source of contamination, in which case exposure of the fuel to said pro-oxidizing sources can be limited appropriately.

When the fuel is in the intermediate oxidation phase, said actions to be carried out are advantageously corrective actions such as adding fresh fuel in order to improve the quality of the product. In one embodiment, the action to be carried out will be to inform the user that rapid use of said fuel in the intermediate oxidation phase is preferable.

When the fuel is in the advanced oxidation phase, said actions to be carried out are, inter alia, warning the user of the distinct risk of using said fuel.

EXAMPLES

Example 1: Development of Classification in Accordance with the Invention

A number of 1 mL samples of fuel were taken after various oxidation times. The samples were analysed using a BRUKER Vertex 70 FTIR (Fourier Transform Infrared Spectroscopy) instrument in a stream of air without $H_2O$/$CO_2$ with a resolution of 2 $cm^{-1}$, DTGS detector, 32 scans par spectrum and using a KBr cell. FIG. 1 shows the change in the FTIR spectra for a model fuel undergoing oxidation. The absorbance peak for the olefins is indicated in the figure by the letter A and the absorbance peak for the oxygenated molecules is indicated in the figure by the letter B. The solid line curve corresponds to an oxidation period equivalent to 0 IP. The dashed line curve corresponds to an oxidation period of 0.5 IP. The bold dotted line curve corresponds to an oxidation period of 1 IP. The feint dotted line curve corresponds to an oxidation period of 1.5 IP. The results are recorded in Table 1.

TABLE 1

| | Oxidation period | | | |
|---|---|---|---|---|
| | 0 IP | 0.5 IP | 1 IP | 1.5 IP |
| Oxygenated molecules content (not oxygenated olefins) (% m/m) | 0% | 1% | 3% | 4.3% |

Thus, in the present example, an oxygenated molecules content of strictly less than 1% corresponds to the period P1, i.e. to a degree of progress of oxidation termed initial in accordance with the invention, an oxygenated molecules content of 1% or more and strictly less than 3% corresponds to the period P2, i.e. to a degree of progress of oxidation termed intermediate in accordance with the invention, and an oxygenated molecules content of 3% or more corresponds to the period P3, i.e. to a degree of progress of oxidation termed advanced in accordance with the invention.

Example 2: Use of Mass Spectroscopy for the Implementation of the Invention

A 1 mL sample of fuel the degree of progress of oxidation of which was to be measured was taken. The sample was analysed using a GC/FID instrument (DB1 column, 60 m, 0.320 mm, 0.25 μm). The chromatogram of FIG. 2 shows the condition of the fresh model fuel; the oxygenated molecules content was 0.0 at 0 IP, i.e. there were no oxidation products present in the fresh product.

Figure 3:
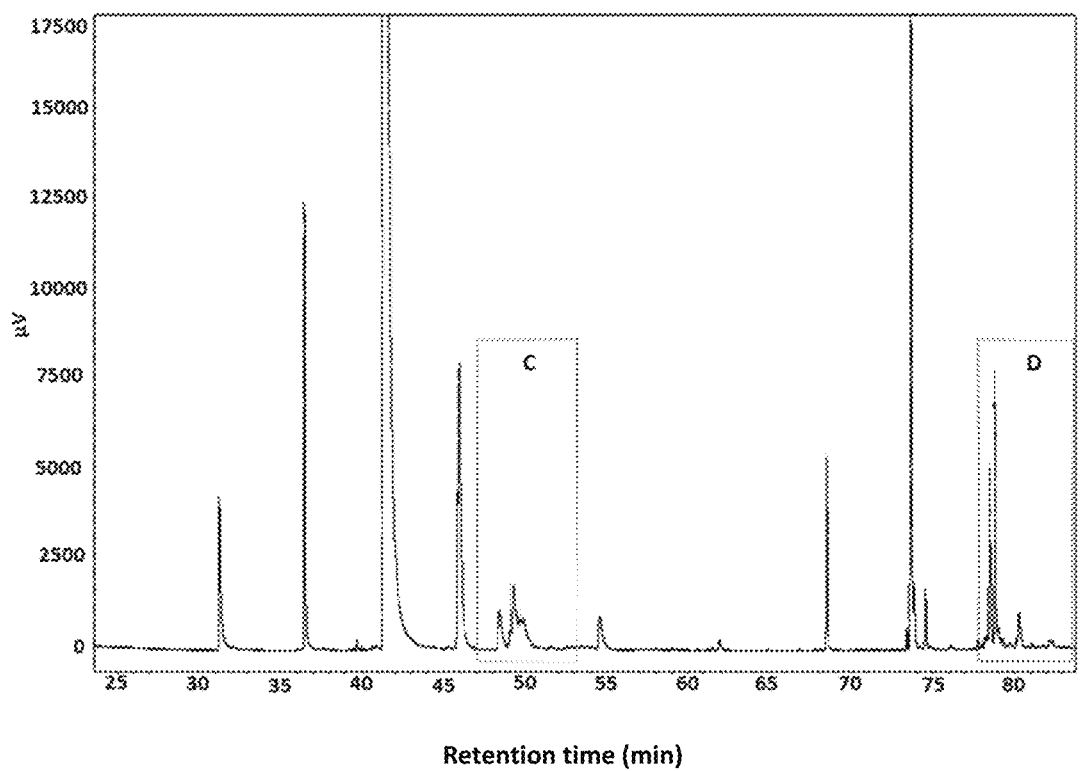
FIG. 3 is a gas phase chromatogram showing the state of the fresh model fuel following an oxidation period.

The chromatogram of FIG. 3 shows the condition of the fuel from which the sample had been taken. The ketones and epoxide contents were measured; the results are recorded in Table 2.

Figure 2:
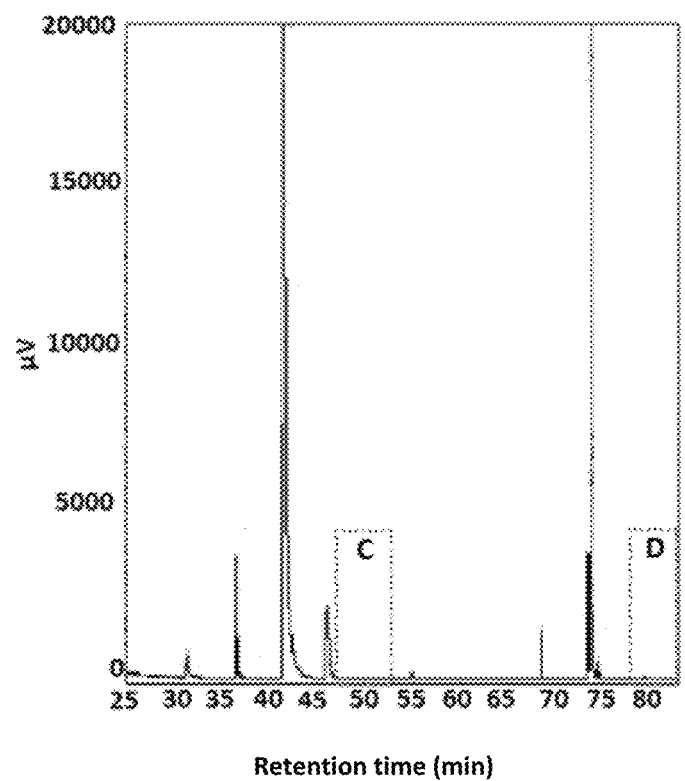
FIG. 2 is a gas phase chromatogram showing the state of a fresh model fuel (mixture of n-paraffins and unsaturated esters) at 0 IP when the fresh model fuel has not yet undergone oxidation.

In the chromatograms of FIGS. 2 and 3, the retention time zone corresponding to the ketones is indicated by the letter C; the retention time zone corresponding to the epoxides is indicated by the letter D.

TABLE 2

| Molecule family | Content (% m/m) |
|---|---|
| Ketones | 3.4 |
| Epoxides | 0.8 |
| Oxygenated molecules (ketones + epoxides) | 4.2 |

The oxygenated molecules contents corresponded to an oxidation period of more than 1 IP. In accordance with the invention, this result corresponds to an oxidation period P3. The fuel of Example 2 was thus classified into the category of "advanced degree of oxidation". The action to be taken was to warn the user of the distinct risk of using the product.

The invention claimed is:

1. A method for continuously monitoring the degree of progress of oxidation of a fuel, comprising at least the following steps:
    a) determining at least one indicator for progress of at least one oxidation reaction to be monitored,
    b) measuring a content of the at least one indicator in the fuel,
    c) classifying the degree of progress of oxidation of the fuel,
    d) determining at least one measure to be taken as a function of the classifying,
    wherein the at least one indicator comprises at least one selected from an intermediate, a final product, and a co-product, of the at least one oxidation reaction with one or more components of the fuel,
    wherein the classifying comprises comparing the measured content of the at least one indicator with a content of the at least one indicator present in the fuel after a period of accelerated oxidation, measured in accordance with the method EN 15751, in order to determine the induction period (IP) for the fuel, the degree of progress of oxidation of the fuel being:
        initial if the measured content corresponds to an oxidation period (P1) strictly less than 0.5 IP (0 IP≤P1<0.5 IP),
        intermediate if the measured content corresponds to an oxidation period (P2) of greater than or equal to 0.5 IP and strictly less than 1 IP (0.5 IP≤P2<IP),
        advanced if the measured content corresponds to an oxidation period (P3) of 1 IP or higher (1 IP≤P3), and
    wherein when the degree of progress of oxidation of the fuel is initial, the at least one measure to be taken comprises at least one selected from an initial corrective action and an initial preventative action,
    when the degree of progress of oxidation of the fuel is intermediate, the at least one measure to be taken comprises an intermediate corrective action, and
    when the degree of progress of oxidation of the fuel is advanced, the at least one measure to be taken comprises warning the user of the distinct risk of using the fuel.

2. The method as claimed in claim 1, wherein the fuel is selected from kerosene, gas oil and gasoline.

3. The method as claimed in claim 1, wherein the progress indicator comprises one or more molecules belonging to families selected from aldehydes, alcohols, ketones, ketoacids, epoxides and carboxylic acids.

4. The method as claimed in claim 1, wherein the progress indicator comprises a molecule selected from families of aldehydes, alcohols, ketones, ketoacids, epoxides and carboxylic acids.

5. The method as claimed in claim 1, wherein the progress indicator comprises formaldehyde or acetaldehyde.

6. The method as claimed in claim 1, wherein the progress indicator comprises ethylene oxide.

7. The method as claimed in claim 1, wherein the co-product comprises one or more polymerized molecules obtained from one or more monomers selected from families of linear alkenes, branched alkenes, aromatics, aldehydes, alcohols, ketones, ketoacids, epoxides and carboxylic acids.

8. The method as claimed in claim 7, wherein the one or more monomers comprises at least one selected from formaldehyde and acetaldehyde.

9. The method as claimed in claim 7, wherein the one or more monomers comprises at least one selected from the family of epoxides.

10. The method as claimed in claim 1, wherein measuring the content of the at least one indicator is carried out by at least one selected from UV, IR, GC, MS, SAXS, and tonometric analysis.

11. The method as claimed in claim 1, wherein the fuel is in the on-board storage phase.

12. The method as claimed in claim 1, wherein the fuel is in the logistical phase.

13. The method as claimed in claim 1, wherein the progress indicator comprises at least one of formaldehyde and acetaldehyde.

14. The method as claimed in claim 1, wherein the initial corrective action comprises adding an anti-oxidizing additive and the initial preventative action comprises eliminating pro-oxidizing sources.

15. The method as claimed in claim 1, wherein the intermediate corrective action comprises adding fresh fuel.

* * * * *